United States Patent
Saint-Ramon et al.

(12) 
(10) Patent No.: US 6,368,786 B1
(45) Date of Patent: Apr. 9, 2002

(54) DILUENT FOR CRYOGENIC STORAGE OF BOVINE SPERMATOZOA

(75) Inventors: Jean-Gérard Saint-Ramon, L'Aigle; Serge Desherches, Vindelle; Gustavo Decuadro-Hansen, Gauville, all of (FR)

(73) Assignee: IMV Technologies, L'Aigle (FR)

( * ) Notice: Subject to any disclaimer, the term of this patent is extended or adjusted under 35 U.S.C. 154(b) by 0 days.

(21) Appl. No.: 09/568,761

(22) Filed: May 11, 2000

(30) Foreign Application Priority Data

May 14, 1999 (FR) .............................. 99 06177

(51) Int. Cl.[7] .............................. A01N 1/02; A61B 17/43
(52) U.S. Cl. .............................. 435/2; 435/1.1; 600/33; 600/35
(58) Field of Search ..................... 435/2, 1.1; 600/33, 600/35

(56) References Cited

U.S. PATENT DOCUMENTS 6,130,034 A * 10/2000 Aitken ........................... 435/2
6,140,121 A * 10/2000 Ellington et al. ........... 435/374

FOREIGN PATENT DOCUMENTS

| EP | 0 685 556 A1 | 5/1995 |
| FR | 2 720 407 | 5/1994 |
| RU | 1189448 A | 11/1985 |

OTHER PUBLICATIONS

Ollero et al., "Improvement of Ram Sperm Cryopreservation Protocols Assessed by Sperm Quality Parameters and Heterogeneity Analysis", Cryobiology 37 : 1–12 (1998).*
Al–Hanak et al., "Effect of Vatamin A on some Bioloical Indexes of bull Spermatozoa on Cryoconservation", Zhivotnov'd Nauki 26 (5) : 80–83 (1989).*
O'Brien et al., "Preservation of Motility in Modeled Bull Sperm Using a Glutathione–Based Antioxidant Medium", J. Cell Biol. 25th Ann. Meeting ASCB 101 (5 part 2) 487A (1985).*
Slaweta et al., "Effect of Glutathione (GSH) on the Quality of Preserved Bull Semen", Med. Weter. 42 (8) : 498–500 (1986).*
Gupta et al., "Comparative Study on Room Temperature Dilutors of Cross–Bred Bull Semen", Indian J. Anim. Res. 18 (2): 81–85 (1984).*
Sanchez–Partida; Setchell; Maxwell; "Epididymal compounds and antioxidants in diluents for the frozen storaged of ram spermatozoa," Reprod. Fertil. Dev., vol. 9, pp. 689–696, (1997).

* cited by examiner

*Primary Examiner*—Sandra E. Saucier
(74) *Attorney, Agent, or Firm*—Morgan & Finnegan, L.L.P.

(57) ABSTRACT

A diluent for the cryogenic storage of bovine spermatozoa includes a phospholipid, a liposoluble vitamin accompanied by an emulsifier, an antioxidant and a polyol.

22 Claims, No Drawings

DILUENT FOR CRYOGENIC STORAGE OF BOVINE SPERMATOZOA

BACKGROUND OF THE INVENTION

1. Field of the Invention

The invention relates to a diluent for cryogenic storage of bovine spermatozoa. More specifically, the invention relates to an aqueous diluent medium which contains no substance of animal origin and which can be stored, ready for use, over prolonged periods.

2. Description of the Prior Art

Diluents for cryogenic storage of bovine spermatozoa are known in the art. FR-B-2 720 407 describes a diluent which contains nutrients, buffers and mineral salts, as well as a protective product consisting of soya lecithin.

The diluent described in the abovementioned patent is intended for diluting bovine semen which is then frozen pending subsequent use. This is an essentially "sanitary" approach. This diluent is relatively satisfactory.

It is easy to prepare and is very clear. The absence of products of animal origin ensures the absence of any infective agent.

However, the question of the biological efficacy of the product was not addressed. The efficacy in the concentration ranges used previously does not provide the flexibility required in an insemination center.

Specifically, it is currently required to optimize the production of semen, i.e. to produce a large number of doses stored in a "French straw" with a minimum concentration of spermatozoa.

In vivo tests with a very low concentration of spermatozoa in the straw indicate that the diluent of FR-B-2 720 407 does not perform well.

One object of the present invention is to provide a diluent for cryogenic storage of bovine spermatozoa which gives improved in vivo results.

Another object of the invention is to provide a diluent which assures satisfactory survival of the spermatozoa at low concentrations.

The present invention provides a diluent which satisfies the above objects.

SUMMARY OF THE INVENTION

The diluent for cryogenic storage of bovine spermatozoa of the present invention includes a phospholipid, a liposoluble vitamin accompanied by an emulsifier, an antioxidant and a polyol.

The vitamin is vitamin A, for example.

The vitamin is accompanied by an emulsifier, for example sorbitan monooleate, which is sold under the trade name Tween 80.

The antioxidant can be an amino acid with anti-oxidant properties, for example taurine or glycine.

The antioxidant can instead be an antioxidant peptide, for example reduced glutathione.

The diluent of the present invention can instead contain a sterol, in particular cholesterol.

When a sterol is present in the diluent, the diluent advantageously contains cyclodextrine which render it soluble in an aqueous medium.

The diluent of the present invention can additionally contain salts and carbohydrates.

The carbohydrates are glucose, fructose or lactose, for example.

The salts are buffers in particular, for example trimethylolmethylamine, which is usually referred to as Tris buffer or simply Tris.

The diluent of the invention contains an effective dose of a polyol capable of inhibiting the formation of ice crystals. The polyol is advantageously glycerol.

To prepare the diluent according to the invention, the following steps are carried out:

a) preparing a dispersion of a phospholipid in the form of particles in a polyol at a sufficient temperature, b) stirring the dispersion from step a) to micronize the phospholipid particles, c) leaving the dispersion obtained in step b) to stand for a period of at least about 12 hours to stabilize the emulsion obtained, i.e. to ensure no separation of phases, yielding a preparation referred to as the preparation from step c), d) preparing an aqueous phase including an amino acid with antioxidant properties, an antioxidant peptide and a vitamin, yielding an aqueous phase referred to as the aqueous phase from step d), e) combining the preparation from step c) and the aqueous phase from step d), yielding a preparation referred to as the preparation from step e), and f) sterilizing the preparation from step e).

According to one preferred embodiment of the invention, the sterilization in step f) is carried out by ionizing radiation in an irradiation dose range from about 5 Kgy to about 20 Kgy, preferably from about 15 Kgy to about 20 Kgy.

Techniques for obtaining the dispersion from step a) include techniques using mechanical dispersants and emulsifiers which act by pressure.

In order to obtain a stable emulsion in step c), it is necessary to leave the dispersion to stand for at least 12 hours.

The diluent of the invention is preferably formulated with a small amount of water and is diluted for use with sterile water.

The diluent advantageously contains an antibiotic agent at the time of use, but if the antibiotic agent is added to the diluent during its preparation, its efficacy can be lost during the sterilization step.

According to one preferred embodiment of the present invention, the antibiotic agent is added extemporaneously at the time of use.

In this embodiment, the antibiotic-free diluent is advantageously contained in a receptacle closed by a stopper. For example, the antibiotic agent in powder form is present in the stopper and is released into the diluent by exerting pressure on the stopper.

The antibiotic agent is gentamycin in sulfate form, for example.

The diluent of the invention typically contains the following phospholipids in the weight proportions indicated below:

"Lecithin 100" having the following weight proportions of the following phospholipids:

phosphatidylcholine 20–24 wt. %
phosphatidylethanolamine 18–22 wt. %
phosphatidylinositol 12–15 wt. %
"Lecithin 130" having the following weight proportions of the following phospholipids:
phosphatidylethanolamine 14–20 wt. %
phosphatidylinositol 7–13 wt. %
phosphatidylcholine 30–35 wt. %
Lecithin 130 is a phosphatidylcholine-enriched lecithin.

It should be noted that the diluent of the invention is intended exclusively for cryogenic storage of bovine spermatozoa. It is not suitable for cryogenic storage of spermatozoa of other animal species or human spermatozoa.

In one preferred embodiment, a diluent according to the invention includes, per 100 ml of water:

| | |
|---|---|
| Tris | 1 to 2 g |
| Trisodium citrate dihydrate | 5 to 10 g |
| Potassium chloride | 0.2 to 0.5 g |
| Fructose | 0.6 to 1.0 g |
| Lactose monohydrate | 0.18 to 0.30 g |
| Glycine | 2.0 to 3.0 g |
| Anhydrous glucose | 0.25 to 0.40 g |
| Taurine | 0.0030 to 0.0040 g |
| Gentamycin sulfate | 0.20 g to 0.30 g |
| Tylosin tartrate | 0.028 to 0.040 g |
| Lincospectin 100 | 0.30 to 0.35 g |
| Glycerol | 30 to 45 g |
| Calcium lactate hydrate | 0.03 to 0.05 g |
| Lecithin 100 | 2.0 to 3.0 g |
| Lecithin 130 | 0.80 to 1.10 g |
| Citric acid monohydrate | 0.5 to 2 g |
| Ultra-pure water | qs |

DETAILED DESCRIPTION OF THE PREFERRED EMBODIMENTS

The examples which follow illustrate the invention in a nonlimiting manner.

EXAMPLE 1

Following the procedure described above, a diluent according to the invention having the composition below was formulated:

| | |
|---|---|
| Tris | 1.8490 g |
| Trisodium citrate dihydrate | 7.3965 g |
| Potassium chloride | 0.2955 g |
| Fructose | 0.8875 g |
| Lactose monohydrate | 0.2220 g |
| Glycine | 2.7735 g |
| Anhydrous glucose | 0.3695 g |
| Taurine | 0.0037 g |
| Gentamycin sulfate | 0.2400 g |
| Tylosin tartrate | 0.0330 g |
| Lincospectin 100 | 0.3830 g |
| Glycerol | 40.2240 g |
| Calcium lactate hydrate | 0.0455 g |
| Lecithin 100 | 2.6000 g |
| Lecithin 130 | 1.0400 g |
| Citric acid monohydrate | 1.0400 g |
| Ultra-pure water | 0.0650 l |

The above formulation produced 100 ml of concentrated diluent which was diluted to 500 ml for use.

EXAMPLE 2

Comparative in vitro tests: anomalies and test of osmotic strength

In this example, the diluent of Example 1 of the invention was compared with the diluent of the prior art described in EP-A-685 556 as regards anomalies and osmotic strength in vitro.

Following the procedure described in EP-A-685 556, a diluent according to the prior art having the composition below was formulated:

| | |
|---|---|
| Trimethylolmethylamine | 3.4 g to 4.2 g |
| Trisodium citrate dihydrate | 13.7 g to 16.75 g |
| Potassium chloride | 0.55 g to 0.67 g |
| Fructose | 1.65 g to 2.0 g |
| Glucose | 0.68 g to 0.84 g |
| Lactose | 0.41 g to 0.50 g |
| Calcium lactate | 0.09 g to 0.11 g |
| Glycine | 5.15 g to 6.25 g |
| Glycerol | 64 ml to 78 ml |
| Soya lecithin | 6.75 g to 8.25 g |

This vehicle was diluted with 750 ml to 900 ml of water prior to use.

Table I gives comparative results for the diluent of the prior art (DILUENT A) and the diluent of the invention (DILUENT I) for various bulls: NIZAGO, NOMEL, NORRIS, NOVAK, OCARINA and OKAVANGO.

TABLE I

| IDENTIFICATION | % major anomalies | % abnormal | HOST |
|---|---|---|---|
| NIZAGO DILUENT A | 12.0% | 23.5% | 51.24% |
| NIZAGO DILUENT I | | | 65.05% |
| NOMEL DILUENT A | 13.5% | 30.0% | 34.31% |
| NOMEL DILUENT I | | | 54.50% |
| NORRIS DILUENT A | 6.0% | 17.5% | 50.50% |
| NORRIS DILUENT I | | | 53.00% |
| NOVAK DILUENT A | 20.0% | 26.0% | 34.80% |
| NOVAK DILUENT I | | | 47.71% |
| OCARINA DILUENT A | 7.5% | 21.0% | 50.00% |
| OCARINA DILUENT I | | | 47.76% |
| OKAVANGO DILUENT A | 8.5% | 18.5% | 67.68% |
| OKAVANGO DILUENT I | | | 67.65% |
| Average results for DILUENT A at $7 \times 10^6$ spz/dose | 11.0% | 23.0% | 48.09% |
| Average results for DILUENT I at $7 \times 10^6$ spz/dose | | | 55.95% |

HOST = osmotic strength test
spz = spermatozoa

Table I clearly indicates the superiority of the diluent of the invention over the diluent of the prior art since, for $7 \times 10^6$ spermatozoa per dose, a very much higher percentage of osmotic strength in vitro is obtained for the diluent of the invention.

EXAMPLE 3

Comparative in vitro tests, results after thawing and temperature resistance test In this example, the diluent of Example 1 of the invention was compared with the diluent of the prior art described in EP-A-685 556 used in Example 2, as regards results after thawing and in vitro temperature resistance.

Table II gives comparative results for the diluent of the prior art (DILUENT A) and the diluent of the invention (DILUENT I) with various bulls: NIZAGO, KOMEL, NORRIS, NOVAK, OCARINA and OKAVANGO.

Table II clearly indicates the superiority of the diluent of the invention over the diluent of the prior art since, for $7 \times 10^6$ spermatozoa per dose, a higher percentage of mobiles and higher motility are obtained, except for the percentage of mobiles during the thawing after 1 h 30, which is very much inferior.

EXAMPLE 4

Comparative in vivo tests: results of in vivo artificial insemination for a nonreturn rate at 25 days In this example, the diluent of Example 1 of the invention was compared with the diluent of the prior art described in EP-A-685 556 used in Example 2, as regards the results of in vivo primary artificial insemination (PAI), fertilization by primary artificial insemination (PAI fert) and percentage of fertilization by primary artificial insemination (% PAI fert), for a nonreturn rate (NRR) at 25 days.

Table III gives comparative results for the diluent of the prior art (DILUENT A) and the diluent of the invention (DILUENT I) with various bulls: NIZAGO, NOMEL, NORRIS, NOVAK, OCARINA and OKAVANGO.

TABLE II

| IDENTIFICATION | Thawing | | TRT + 30 min | | TRT + 1 h 30 | | Thawing | | TRT 1 h to 1 h 45 | |
|---|---|---|---|---|---|---|---|---|---|---|
| | % mobiles | Motility | % mobiles | Motility | % mobiles | Motility | % mobiles | Motility | % mobiles | Motility |
| NIZAGO DILUENT A | 55% | 3 | 50% | 2 | 30% | 1.5 | 55% | 3 | 0% | 0 |
| NIZAGO DILUENT I | 55% | 3.5 | 55% | 3 | 45% | 2 | 55% | 3 | 45% | 2 |
| NOMEL DILUENT A | 55% | 3.5 | 55% | 3 | 10% | 1 | 45% | 3 | 35% | 3 |
| NOMEL DILUENT I | 45% | 3 | 45% | 2 | 10% | 0.5 | 45% | 3 | 40% | 3 |
| NORRIS DILUENT A | 40% | 2 | 40% | 1 | 10% | 0.5 | 50% | 2.5 | 0% | |
| NORRIS DILUENT I | 45% | 3 | 45% | 2 | 45% | 3 | 30% | 3 | 5% | |
| NOVAK DILUENT A | 30% | 2 | 30% | 1.5 | 10% | 0.5 | 45% | 2.5 | 0% | |
| NOVAK DILUENT I | 35% | 3 | 35% | 2.5 | 35% | 3 | 40% | 3.5 | 0% | |
| OCARINA DILUENT A | 55% | 3.5 | 50% | 3 | 50% | 3 | 45% | 3 | 5% | |
| OCARINA DILUENT I | 60% | 3.5 | 55% | 3 | 50% | 3.5 | 55% | 4 | 10% | |
| OKAVANGO DILUENT A | 55% | 3.5 | 45% | 2.5 | 30% | 2 | 55% | 3 | 45% | 2.5 |
| OKAVANGO DILUENT I | 55% | 3.5 | 60% | 3.5 | 50% | 3 | 55% | 3 | 45% | 3 |
| Average results for DILUENT A at $7 \times 10^4$ spz/dose | 48% | 2.92 | 45% | 2.17 | 23% | 1.42 | 49% | 2.83 | 14% | 1.50 |
| Average results for DILUENT I at $7 \times 10^6$ spz/dose | 49% | 3.25 | 49% | 2.67 | 39% | 2.50 | 47% | 3.25 | 24% | 2.67 |

TRT = temperature resistance test
spz = spermatozoa

TABLE III

| | NRR at 25 days | | | | | | | | | | |
|---|---|---|---|---|---|---|---|---|---|---|---|
| IDENTIFICATION | PAI | PAI fert | % PAI fert | AI2 | AI2 fert | % IA2 fert | IA3+ | AI3 + fert | % AI3 + fert | Total AI | Total AI fert | Total % AI fert |
| NIZAGO DILUENT A | 66 | 44 | 66.67% | 48 | 35 | 72.92% | 74 | 55 | 74.32% | 188 | 134 | 71.28% |
| NIZAGO DILUENT I | 68 | 55 | 80.88% | 33 | 27 | 81.82% | 89 | 71 | 79.78% | 190 | 153 | 80.53% |
| NOMEL DILUENT A | 76 | 60 | 78.95% | 45 | 37 | 82.22% | 71 | 59 | 83.10% | 192 | 156 | 81.25% |
| NOMEL DILUENT I | 72 | 59 | 81.94% | 48 | 40 | 83.33% | 72 | 60 | 83.33% | 192 | 159 | 82.81% |
| NORRIS DILUENT A | 74 | 61 | 82.43% | 42 | 31 | 73.81% | 75 | 56 | 74.67% | 191 | 148 | 77.49% |
| NORRIS DILUENT I | 60 | 51 | 85.00% | 41 | 33 | 80.49% | 73 | 54 | 73.97% | 174 | 138 | 79.31% |
| NOVAK DILUENT A | 80 | 63 | 78.75% | 34 | 31 | 91.18% | 63 | 50 | 79.37% | 177 | 144 | 81.36% |
| NOVAK DILUENT I | 68 | 52 | 76.47% | 50 | 45 | 90.00% | 77 | 67 | 87.01% | 195 | 164 | 84.10% |
| OCARINA DILUENT A | 73 | 60 | 82.19% | 41 | 38 | 92.68% | 73 | 60 | 82.19% | 187 | 158 | 84.49% |
| OCARINA DILUENT I | 72 | 65 | 90.28% | 47 | 37 | 78.72% | 74 | 59 | 79.73% | 193 | 161 | 83.42% |
| OKAVANGO DILUENT A | 74 | 57 | 77.03% | 34 | 29 | 85.29% | 60 | 49 | 81.67% | 168 | 135 | 80.36% |
| OKAVANGO DILUENT I | 71 | 52 | 73.24% | 47 | 39 | 82.98% | 75 | 63 | 84.00% | 193 | 154 | 79.79% |
| Average results for Diluent A at $7 \times 10^6$ spz/dose | 443 | 345 | 77.88% | 244 | 201 | 82.38% | 416 | 329 | 79.09% | 1103 | 875 | 79.33% |
| Average results for Diluent I at $7 \times 10^6$ spz/dose | 411 | 334 | 81.27% | 266 | 221 | 83.08% | 460 | 374 | 81.30% | 1137 | 929 | 81.71% |
| Average results for the test bulls over the same period at $20 \times 10^6$ spz/dose DILUENT A | 2028 | 1630 | 80.37% | | | | | | | | | |

NRR = nonreturn rate
spz = spermatozoa

Table III clearly indicates the superiority of the diluent of the invention over the diluent of the prior art, since a very much higher percentage PAI is obtained in all cases but one (for the bull OKAVANGO). The average results for 7×10$^6$ spermatozoa per dose reveal a very much higher PAI percentage for the diluent of the invention.

Surprisingly, the diluent of the prior art shows very inferior average results, even for 20×10$^6$ spermatozoa per dose, than the diluent of the invention for only 7×10$^6$ spermatozoa per dose.

EXAMPLE 5

Comparative in vivo tests: results of in vivo artificial insemination for a nonreturn rate at 60 days In this Example, the diluent of Example 1 of the invention was compared with the diluent of the prior art described in EP-A-685 556 used in Example 2, as regards the results of in vivo primary artificial insemination (PAI), fertilization by primary artificial insemination (PAI fert) and percentage of fertilization by primary artificial insemination (% PAI fert), for a nonreturn rate (NRR) at 60 days.

Table IV gives comparative results for the diluent of the prior art (DILUENT A) and the diluent of the invention (DILUENT I) with various bulls: NIZAGO, NOMEL, NORRIS, NOVAK, OCARINA and OKAVANGO.

Surprisingly, the diluent of the invention even has, for only 7×10$^6$ spermatozoa per dose, average results that are better than those for the diluent of the prior art for 20×10$^6$ spermatozoa per dose.

TABLE IV

| | NRR at 60 days | | | | | | | | | | |
|---|---|---|---|---|---|---|---|---|---|---|---|
| IDENTIFICATION | PAI | PAI fert | % PAI fert | AI2 | AI2 fert | % IA2 fert | IA3+ | AI3 + fert | % AI3 + fert | Total AI | Total AI fert | Total % AI fert |
| NIZAGO DILUENT A | 55 | 24 | 43.64% | 40 | 15 | 37.50% | 68 | 39 | 57.35% | 163 | 78 | 47.85% |
| NIZAGO DILUENT I | 68 | 40 | 58.82% | 33 | 22 | 66.67% | 87 | 60 | 68.97% | 188 | 122 | 64.89% |
| NOMEL DILUENT A | 72 | 41 | 56.94% | 43 | 27 | 62.79% | 64 | 41 | 64.06% | 179 | 109 | 60.89% |
| NOMEL DILUENT I | 62 | 38 | 61.29% | 38 | 24 | 63.16% | 63 | 36 | 57.14% | 163 | 98 | 60.12% |
| NORRIS DILUENT A | 69 | 39 | 56.52% | 41 | 24 | 58.54% | 72 | 40 | 55.56% | 182 | 103 | 56.59% |
| NORRIS DILUENT I | 55 | 35 | 63.64% | 34 | 19 | 55.88% | 65 | 38 | 58.46% | 154 | 92 | 59.74% |
| NOVAK DILUENT A | 61 | 36 | 59.02% | 47 | 37 | 78.72% | 72 | 47 | 65.28% | 180 | 120 | 66.67% |
| NOVAK DILUENT I | 74 | 44 | 59.46% | 30 | 21 | 70.00% | 57 | 37 | 64.91% | 161 | 102 | 63.35% |
| OCARINA DILUENT A | 44 | 27 | 61.36% | 31 | 24 | 77.42% | 53 | 35 | 66.04% | 128 | 86 | 67.19% |
| OCARINA DILUENT I | 68 | 50 | 73.53% | 44 | 28 | 63.64% | 72 | 46 | 63.89% | 184 | 124 | 67.39% |
| OKAVANGO DILUENT A | 39 | 26 | 66.67% | 23 | 15 | 65.22% | 42 | 27 | 64.29% | 104 | 68 | 65.38% |
| OKAVANGO DILUENT I | 70 | 36 | 51.43% | 46 | 29 | 63.04% | 75 | 52 | 69.33% | 191 | 117 | 61.26% |
| Average results for Diluent A at 7 × 10$^6$ spz/dose | 340 | 193 | 56.76% | 225 | 142 | 63.11% | 371 | 229 | 61.73% | 936 | 564 | 60.26% |
| Average results for Diluent I at 7 × 10$^6$ spz/dose | 397 | 243 | 61.23% | 225 | 143 | 63.56% | 419 | 269 | 64.20% | 1041 | 655 | 62.92% |
| Average results for the test bulls over the same period at 20 × 10$^6$ spz/dose DILUENT A | 1771 | 1097 | 61.94% | | | | | | | | | |

NRR = nonreturn rate
spz = spermatozoa

EXAMPLE 6

Comparative in vivo tests: results of in vivo artificial insemination for a nonreturn rate at 90 days In this example, the diluent of Example 1 of the invention was compared with the diluent of the prior art described in EP-A-685 556 used in Example 2, as regards the results of in vivo primary artificial insemination (PAI), fertilization by primary artificial insemination (PAI fert) and percentage of fertilization by primary artificial insemination (% PAI fert), for a nonreturn rate (NRR) at 90 days.

Table V gives comparative results for the diluent of the prior art (DILUENT A) and the diluent of the invention (DILUENT I) with different bulls: NIZAGO, NOMEL, NORRIS, NOVAK, OCARINA and OKAVANGO.

Table V clearly indicates the superiority of the diluent of the invention over the diluent of the prior art, since a higher percentage of PAI is obtained in all cases but one (for the OKAVANGO bull). The average results for 7×10⁶ spermatozoa per dose reveal a markedly higher percentage of PAI for the diluent of the invention.

Surprisingly, the diluent of the invention even shows, for only 7×10⁶ spermatozoa per dose, average results that are higher than those for the diluent of the prior art for 20×10⁶ spermatozoa per dose.

Although the invention has been described for specific embodiments, it will be understood that it encompasses all the implementation variants in the scope of the claims.

TABLE V

| | NRR at 90 days | | | | | | | | | | |
|---|---|---|---|---|---|---|---|---|---|---|---|
| IDENTIFICATION | PAI | PAI fert | % PAI fert | AI2 | AI2 fert | % IA2 fert | IA3+ | AI3 + fert | % AI3 + fert | Total AI | Total AI fert | Total % AI fert |
| NIZAGO DILUENT A | 65 | 24 | 36.92% | 47 | 19 | 40.43% | 74 | 35 | 47.30% | 186 | 78 | 41.94% |
| NIZAGO DILUENT I | 68 | 37 | 54.41% | 33 | 19 | 57.58% | 89 | 55 | 61.80% | 190 | 111 | 58.42% |
| NOMEL DILUENT A | 76 | 36 | 47.37% | 45 | 24 | 53.33% | 71 | 42 | 59.15% | 192 | 102 | 53.13% |
| NOMEL DILUENT I | 72 | 37 | 51.39% | 48 | 22 | 45.83% | 72 | 38 | 52.78% | 192 | 97 | 50.52% |
| NORRIS DILUENT A | 74 | 37 | 50.00% | 42 | 23 | 54.76% | 75 | 37 | 49.33% | 191 | 97 | 50.79% |
| NORRIS DILUENT I | 60 | 31 | 51.67% | 41 | 21 | 51.22% | 73 | 42 | 57.53% | 174 | 94 | 54.02% |
| NOVAK DILUENT A | 68 | 33 | 48.53% | 50 | 35 | 70.00% | 77 | 43 | 55.84% | 195 | 111 | 56.92% |
| NOVAK DILUENT I | 78 | 41 | 52.56% | 32 | 23 | 71.88% | 62 | 38 | 61.29% | 172 | 102 | 59.30% |
| OCARINA DILUENT A | 72 | 42 | 58.33% | 41 | 25 | 60.98% | 73 | 49 | 67.12% | 186 | 116 | 62.37% |
| OCARINA DILUENT I | 72 | 46 | 63.89% | 47 | 27 | 57.45% | 74 | 42 | 56.76% | 193 | 115 | 59.59% |
| OKAVANGO DILUENT A | 73 | 37 | 50.68% | 34 | 20 | 58.82% | 60 | 34 | 56.67% | 167 | 91 | 54.49% |
| OKAVANGO DILUENT I | 71 | 31 | 43.66% | 47 | 29 | 61.70% | 75 | 47 | 62.67% | 193 | 107 | 55.44% |
| Average results for Diluent A at 7 × 10⁶ spz/dose | 428 | 209 | 48.83% | 259 | 146 | 56.37% | 430 | 240 | 55.81% | 1117 | 595 | 53.27% |
| Average results for Diluent I at 7 × 10⁶ spz/dose | 421 | 223 | 52.97% | 248 | 141 | 56.85% | 445 | 262 | 58.99% | 1114 | 626 | 56.19% |
| Average results for the test bulls over the same period at 20 × 10⁶ spz/dose DILUENT A | 1833 | 1009 | 55.05% | | | | | | | | | |

NRR = nonreturn rate
spz = spermatozoa

There is claimed:

1. A diluent for cryogenic storage of bovine spermatozoa, comprising a phospholipid, a liposoluble vitamin accompanied by an antioxidant and a polyol, wherein said vitamin is vitamin A, said diluent further comprising a sterol and cyclodextrins to render said sterol soluble.

2. The diluent claimed in claim 1 in which said antioxidant is an amino acid with antioxidant properties.

3. The diluent claimed in claim 2 in which said amino acid with antioxidant properties is taurine.

4. The diluent claimed in claim 1 in which said antioxidant is an antioxidant peptide.

5. The diluent claimed in claim 4 in which said antioxidant peptide is reduced glutathione.

6. The diluent claimed in claim 1 in which said sterol is cholesterol.

7. The diluent claimed in claim 1 wherein said polyol is glycerol.

8. The diluent claimed in claim 1 further including salts and carbohydrates.

9. A process for preparing a diluent for cryogenic storage of bovine spermatozoa, comprising a phospholipid, a liposoluble vitamin accompanied by an antioxidant peptide or amino acid with antioxidant properties, and a polyol, including the following steps:

a) preparing a dispersion of a phospholipid in the form of particles in a polyol;

b) stirring the dispersion from step a) to micronize said phospholipid particles;

c) leaving the dispersion obtained in step b) to stand for a period of at least about 12 hours to stabilize the emulsion obtained, yielding a preparation referred to as the preparation from step c), d) preparing an aqueous phase including an amino acid with antioxidant properties or an antioxidant peptide, and a liposoluble vitamin, yielding a phase referred to as the aqueous phase from step d), e) combining said preparation from step c) and said aqueous phase from step d), yielding a preparation referred to as the preparation from step e), and f) sterilizing said preparation from step e).

10. The process claimed in claim 9 wherein said sterilization in step f) is carried out by ionizing radiation in an irradiation dose range from about 5 Kgy to about 20 Kgy.

11. The process claimed in claim 10 wherein said irradiation dose range is from about 15 Kgy to about 20 Kgy.

12. The process claimed in claim 10 for preparing the diluent claimed in claim 9 wherein a sterol is added to said preparation from step d).

13. The process claimed in claim 10 for preparing the diluent claimed in claim 11 wherein carbohydrates are added to said preparation from step d).

14. The process of claim 9 wherein said antioxidant is an amino acid with antioxidant properties.

15. The process of claim 14 wherein said amino acid with antioxidant properties is taurine.

16. The process of claim 9 wherein said antioxidant is an antioxidant peptide.

17. The process of claim 16 wherein said antioxidant peptide is glutathione.

18. The process of claim 9 wherein said vitamin is vitamin A.

19. The process of claim 9 wherein said diluent further comprises a sterol.

20. The process of claim 19 wherein said diluent further comprises cyclodextrins to render said sterol soluble.

21. The process of claim 9 wherein said wherein said polyol is glycerol.

22. The process of claim 9 wherein said diluent further comprises salts and carbohydrates.

* * * * *